United States Patent [19]

Jain et al.

[11] Patent Number: 4,610,870

[45] Date of Patent: Sep. 9, 1986

[54] CONTROLLED RELEASE FORMULATION

[75] Inventors: Nemichand B. Jain, Monmouth Junction; Linda P. Gertie, Cinnaminson; Edward M. Rudnic, Plainsboro, all of N.J.

[73] Assignee: E. R. Squibb & Sons, Inc., Princeton, N.J.

[21] Appl. No.: 658,005

[22] Filed: Oct. 5, 1984

[51] Int. Cl.$^4$ .......................... A61K 9/22; A61K 9/24
[52] U.S. Cl. ........................... 424/19; 424/21; 424/22; 424/35
[58] Field of Search ..................... 424/19–22, 424/35

[56] References Cited

U.S. PATENT DOCUMENTS

| | | | |
|---|---|---|---|
| 2,887,440 | 5/1959 | Greminger et al. | 424/35 |
| 3,065,143 | 4/1960 | Christenson et al. | 167/82 |
| 3,427,378 | 2/1969 | Henderson et al. | 424/14 |
| 3,444,290 | 5/1969 | Wal et al. | 424/4 |
| 3,458,622 | 3/1969 | Hill | 424/19 |
| 3,555,151 | 1/1971 | Kaplan et al. | 424/156 |
| 3,574,820 | 4/1971 | Johnson et al. | 424/32 |
| 3,976,764 | 8/1976 | Watanabe et al. | 424/19 |
| 4,140,755 | 2/1979 | Sheth | 424/21 |
| 4,173,626 | 11/1979 | Dempski et al. | 424/19 |
| 4,248,857 | 2/1981 | DeNeale et al. | 424/21 |
| 4,252,786 | 2/1981 | Weiss et al. | 424/19 |
| 4,259,314 | 3/1981 | Lowey | 424/19 |
| 4,309,404 | 1/1982 | DeNeale et al. | 424/21 |
| 4,309,405 | 1/1982 | Guley et al. | 424/21 |
| 4,389,393 | 6/1983 | Schor et al. | 424/19 |
| 4,505,890 | 3/1985 | Jain et al. | 424/35 |
| 4,555,399 | 11/1985 | Hsiao | 424/35 |

*Primary Examiner*—Shep K. Rose
*Attorney, Agent, or Firm*—Lawrence S. Levinson; Burton Rodney

[57] ABSTRACT

A controlled release pharmaceutical formulation which undergoes substantially or approaches zero order release of active drug is provided, preferably in the form of a coated tablet, containing a core portion from which medicament, such as procainamide hydrochloride, is slowly released over a controlled length of time. The core also includes one or more hydrocolloid gelling agents having a viscosity of within the range of from about 10,000 to about 200,000 centipoises in 2% solution at 20° C., such as hydroxypropylmethyl cellulose and/or methyl cellulose, one or more non-swellable binders and/or wax binders (where the medicament and/or hydrocolloid gelling agents are non-compressible), one or more inert fillers or excipients, one or more lubricants, and optionally one or more anti-adherents such as silicon dioxide and water. The above-described core is coated with a pharmaceutical coating composition containing a hydrophobic polymer and a hydrophilic polymer.

16 Claims, No Drawings

CONTROLLED RELEASE FORMULATION

Field of the Invention

The present invention relates to a controlled release formulation, preferably in the form of a tablet, for slowly releasing medicament, such as the cardiac depressant (anti-arrhythmic) procainamide hydrochloride.

BACKGROUND OF THE INVENTION

It is of great advantage to both the patient and clinician that medication be formulated so that it may be administered in a minimum number of daily doses from which the drug is uniformly released over a desired extended period of time. Until now, this has been accomplished in several different ways. Medicinal agents are either coated with varying thicknesses of a relatively insoluble material or are embedded into a rigid lattice of resinous material. The medicinal agent is continuously made available for absorption into the blood stream to replace the amount eliminated while the dosage form is passing through the gastrointestinal tract of the patient. However, certain types of medicinal agents are not suited to absorption during passage through the gastrointestinal tract. For example, most acidic medicinals are principally absorbed from the stomach, whereas most basic medicinals are absorbed primarily from the intestines.

U.S. Pat. No. 3,458,622 to Hill discloses a controlled release tablet for the administration of medicinal agents over a prolonged period of up to about eight hours. This patent discloses a compressed tablet for the prolonged release of a medicament containing that medicament in a core formed from a polymeric vinyl pyrrolidone, preferably polyvinyl pyrrolidone (PVP), and a carboxyvinyl hydrophilic polymer (hydrocolloid) such as those marketed under the trademark Carbopol. The core material formed from the two polymeric substances provides the controlled release effect by forming a complex under the action of water or gastric fluid. This complex is gel-like in consistency and retards the diffusion of active ingredient from the tablet. The controlled release rate of the drug is dependent upon the interaction of the two principal ingredients, the polymer and the hydrocolloid, in the presence of water to form a gummy complex of low solubility. Since little of the gummy complex is present initially, the drug at or near the surface dissolves farily rapidly and there is an initial surge wherein a relatively large amount of drug is released in the beginning for a period of about one hour. As the colloid complex is formed, once aqueous solution penetrates the surface of the tablet, the gel retards the dissolution of the drug out of the tablet.

U.S. Pat. No. 4,252,786 to Weiss et al recognizes the initial surge problem in the Hill patent and resolves same by applying a rupturable relatively water-insoluble water-permeable film formed of a combination of hydrophobic and hydrophilic polymers over an insoluble swelling type delayed release matrix or core containing the medicament which core includes a blend of polyvinyl pyrrolidone and a carboxyvinyl hydrophilic polymer. Weiss et al in Column 2 states as follows:

"Initially, while the film is intact, the release of the drug contained in the matrix is primarily controlled by diffusion of solvent and solute molecules through the film. As water or gastric fluid permeates through the film, the gummy complex forms and the slight swelling of the complex causes the film to rupture or erode. The release rate is then controlled by the gummy complex. The application of a relatively water insoluble, water permeable film primarily controls the drug release rate while the matrix gel is being generated and a smoother, gradual, more uniform release rate is achieved during the entire period of about eight to twelve hours, approaching a zero order release pattern. The release pattern of the core, upon application of the film, can be varied over a range by varying the composition and amount of film-forming mixture."

U.S. Pat. No. 4,140,755 to Sheth et al discloses a sustained release formulation in the form of sustained release tablets which are hydrodynamically balanced to have a bulk density (specific gravity) of less than 1 in contact with gastric fluid and which will therefore remain floating in gastric fluid which has a specific gravity of between 1.004 and 1.010. The Sheth et al sustained release formulation contains a homogeneous mixture of one or more medicaments with one or more hydrophilic hydrocolloids, such as hydroxypropyl methyl cellulose having a viscosity of 4000 cps. The hydrocolloids when contacted with gastric fluid at body temperatures form a sustained gelatinous mix on the surface of the tablet causing the tablet to enlarge and acquire a bulk density of less than 1. The medicament is slowly released from the surface of the gelatinous mix which remains buoyant in the gastric fluid.

All of the medicament in the tablet disclosed in the Sheth et al patent is released in the stomach.

U.S. Pat. Nos. 4,309,404 and 4,248,857 to DeNeale et al disclose slow release formulations for many different drugs and classes of drugs including propranolol and other antihypertensives which formulations are formed of a core material containing the active drug (31–53%), carboxypolymethylene (7–14.5%), zinc oxide (0–3%), stearic acid (4.5 to 10%) and mannitol (3 to 30%); a seal coating surrounding the core; and a sugar coating surrounding the seal coating.

U.S. Pat. No. 4,309,405 to Guley et al discloses a sustained release tablet similar to that disclosed in DeNeale et al (4,309,404) except that the core contains 20 to 70% drug, 30 to 72% of a mixture of a water-soluble polymer such as hydroxypropylmethyl cellulose or hydroxypropyl cellulose and water-insoluble polymer (ethylcellulose alone or in admixture with carboxypolymethylene, hydroxypropyl cellulose and the like).

Each of the DeNeale et al and Guley et al patents disclose that their compositions provide substantially zero order release of the core contained drug for about 12 hours following the first hour of administration. Thus, zero order release is only obtained after the initial surge of release of drug in the first hour.

U.S. Pat. No. 4,259,314 to Lowey discloses a controlled long-acting dry pharmaceutical composition which includes a dry carrier formed from a mixture of hydroxypropylmethyl cellulose (viscosity of 50 to 4000 cp in 2% aqueous solution at 20° C.) and hydroxypropyl cellulose (viscosity of 4000 to 6500 cp for a 2% aqueous solution at 25° C.) which dry carrier is employed with a therapeutic agent among which include aspirin, ascorbic acid and nitroglycerin.

U.S. Pat. Nos. 3,065,143 to Christenson et al, U.S. Pat. No. 3,147,137 to Playfair, U.S. Pat. No. 3,444,290 to Wal et al, U.S. Pat. No. 3,427,378 to Henderson et al, U.S. Pat. No. 3,555,151 to Kaplan et al, U.S. Pat. No. 3,574,820 to Johnson et al, and U.S. Pat. No. 3,976,764 to Watanabe and U.S. Pat. No. 4,173,626 to Dempski et al disclose various sustained release tablets which include gelling agents none of which includes as the active ingredient an angiotensin converting enzyme inhibitor.

U.S. Pat. No. 4,389,393 to Schor et al dicloses a carrier base material to be combined with a therapeutically active medicament into a solid dosage form. The carrier base material is one or more hydroxypropylmethyl celluloses, or a mixture of one or more hydroxypropylmethyl celluloses and up to 30% by weight of the mixture of methyl cellulose, sodium carboxymethyl cellulose and/or other cellulose ether, wherein at least one of the hydroxypropylmethyl celluloses has an average molecular weight of at least 50,000, the carrier base material constituting less than one-third of the weight of the solid unit dosage form.

DESCRIPTION OF THE INVENTION

In accordance with the present invention, a controlled release formulation for the time release of medicament, preferably in the form of a tablet, is provided, which is exceptional in that it is capable of high drug loading and as a release mechanism for substantially zero order release of medicaments, such as procainamide hydrochloride, over a period of 10 to 12 hours or more substantially starting from ingestion of the tablet. The controlled release formulation of the invention is in the form of a coated tablet which includes a core containing the medicament, one or more water-soluble or water-swellable hydrocolloid gelling agents having a viscosity of within the range of from about 10,000 to about 200,000 centipoises in 2% aqueous solution at 20° C., optionally one or more non-swellable binders and/or waxes where the medicament and/or hydrocolloid gelling agent is non-compressible, and one or more lubricants, and optionally one or more anti-adherents, water and/or other conventional additives. The core will be coated with a unique pharmaceutically acceptable coating which will include a combination of water-insoluble film-former and water-soluble film-former, one or more plasticizers, one or more solvents and other conventional ingredients.

The term "non-compressible" as employed herein refers to the inability of medicament and/or hydrocolloid gelling agent to form a compact with a hardness of 8 Strong-Cobb units (SCU) under a pressure of 1000 or more newtons of force.

Upon oral ingestion of the sustained release tablet of the invention, the tablet coating first slowly peels off up to hours after ingestion, leaving the core contents in contact with gastric fluid. Upon contact with gastric fluid, the core very slowly erodes; the outermost hydrocolloid particles hydrate and swell to form a gelatinous mass which acts as a protective barrier. Medicament is released by diffusion or leaching through the gel layer. In fact, the medicament is released practically uniformly over a period of 10 to 12 hours or more in a substantially linear or zero order release essentially starting from ingestion to provide substantially the same therapeutic efficacy for the drug as provided by the identical dosage of drug administered in divided doses.

It has been found that zero order release of the medicament from the uncoated core is not possible but it is only through the presence of the unique coating in combination with the unique core formulation that near zero order or linear release is obtained.

In addition, it has also been found that the controlled release formulation of the invention, for example, in the form of a tablet, allows for surprisingly high drug loading. Thus, until now whereas in conventional procainamide hydrochloride formulations, due to the high water-solubility of the drug, it has been possible to include a core formulation containing at most 65% procainamide hydrochloride based on the weight of the core through the use of the unique combination of coating and core of the present invention, it is now possible to achieve a core formulation containing 80 to 95% procainamide hydrochloride based on the weight of the core. Thus, in effect, the controlled release formulations of the invention may contain from about 14 to 28% or more procainamide hydrochloride than prior art formulations thereby allowing for a reduction in number of daily doses and longer release rates as compared to prior art formulations.

As indicated, the unique core-coating combination in the tablets of the invention allow for unexpectedly high drug loading, Thus, the medicament may be present in the core in an amount of more than about 70% by weight of the core and preferably in an amount within the range of from more than about 75 to about 93% and more preferably, of from about more than 75 to about 85% by weight of the core.

A wide variety of medicaments which are orally administered in tablet form can be used in the form of tablets prepared according to this invention. These include, for example, adrenergic agents such as ephedrine, desoxyephedrine, phenylephrine, epinephrine and the like, cholinergic agents such as physostigmine, neostigmine and the like, antispasmodic agents such as atropine, methantheline, papaverine and the like, curariform agents such as chlorisondamine and the like, tranquilizers and muscle relaxants such as fluphenazine, chlorpromazine, triflupromazine, mephenesin, meprobamate and the like, antidepressants like amitriptyline, nortriptyline, and the like, antihistamines such as diphenhydramine, dimenhydrinate, tripelennamine, perphenazine, chlorprophenazine, chlorprophenpyridamine and the like, hypotensive agents such as rauwolfia, reserpine and the like, cardioactive agents such as bendroflumethiazide, flumethiazide, chlorothiazide, aminotrate, propranolol, nadolol, procainamide and the like, angiotensin converting enzyme inhibitors such as captopril and enalapril, bronchodialators such as theophylline, steroids such as testosterone, prednisolone, and the like, antibacterial agents, e.g., sulfonamides such as sulfadiazine, sulfamerazine, sulfamethazine, sulfisoxazole and the like, antimalarials such as chloroquine and the like, antibiotics such as the tetracyclines, nystatin, streptomycin, cephradine and other cephalosporins, penicillin, semi-synthetic penicillins, griseofulvin and the like, sedatives such as chloral hydrate, phenobarbital and other barbiturates, glutethimide, antitubercular agents such as isoniazid and the like, analgesics such as aspirin, acetominophen, propoxyphene, meperidine and the like, etc. These substances are frequently employed either as the free compound or in a salt form, e.g., acid addition salts, basic salts like alkali metal salts, etc. Other therapeutic agents having the same or different physiological activity can also be employed in pharmaceutical preparations within the scope of the present invention.

The invention is particularly adapted for controlled release tablets containing the antiarrhythmic agent procainamide (usually formulated in the form of its hydrochloride).

The hydrocolloid gelling agent, may be of the compressible or non-compressible type, and is esential to the practice of the invention in that it absorbs water, swells and forms a gel. It will be of the type to provide a viscosity of 10,000 to 200,000 centipoises in a 2% aqueous solution at 20° C., will have a molecular weight ranging from about 80,000 to about 300,000, and will be present in an amount small enough to ensure that a near zero order release is obtained, at a sufficient rate, not only after the first hour, but substantially immediately after ingestion. Thus, the hydrocolloid is provided in an amount within the range of from about 5 to about 15% by weight of the core and preferably from about 5 to about 12%. Although amounts of hydrocolloid of higher than 15% by weight may be employed, the rate of release of drug may be undesirably slowed down.

The hydrocolloid for use in the core will have a viscosity of more than 10,000 centipoises as indicated above, and will preferably comprise cellulose polymers which are cellulose ethers such as methyl cellulose, cellulose alkyl hydroxylates such as hydroxypropylmethyl cellulose, hydroxypropyl cellulose, hydroxymethyl cellulose or hydroxyethyl cellulose, cellulose alkyl carboxylates such as carboxymethyl cellulose and carboxyethyl cellulose, and alkali metal salts of cellulose alkyl carboxylates, such as sodium carboxymethyl cellulose and sodium carboxyethyl cellulose, as well as carboxypolymethylene (molecular weight 2.5 to 3.5 million). Preferred are sodium carboxymethyl cellulose, methyl cellulose, hydroxypropylmethyl cellulose and carboxypolymethylene. However, it is to be understood that any hydrocolloid may be employed in the present invention, such as, for example, gum acacia, guar gum, gum tragacanth, gum xanthan, an alkali metal or alkaline earth metal carageenate, alginates, such as alginic acid, ammonium or sodium alginate or mixtures thereof.

Other examples of suitable hydrocolloids are set out in U.S. Pat. No. 4,140,755 to Sheth et al.

Where both the medicament and/or the hydrocolloid gelling agent are non-compressible, it is preferred that the core also include one or more non-swellable binders which bind the core ingredients to prevent premature core disintegration and promote proper release rate. The binders will be present in the core in an amount within the range of from 0 to about 8% and preferably from about 2 to about 5% by weight of the core. Examples of such binders suitable for use herein include, but are not limited to, polyvinylpyrrolidone (molecular weight ranging from 5000 to 80,000 and preferably about 40,000), lactose, gelatin, starches such as corn starch, modified corn starch, sugars, gum acacia and the like.

In addition to, or in lieu of, the above described non-swellable binders, the core may contain a wax binder in finely powdered form of average particle size of, for example, less than 500 microns and preferably within the range of from about 150 to about 500 microns, in an amount within the range of from 0 to about 8% and preferably from about 2 to about 5% by weight of the core. Examples of such wax binders suitable for use herein include, but are not carnauba wax, paraffin, spermaceti, polyethylenes or microcrystalline wax.

It will be appreciated that at least one of the non-swellable binders, preferably, polyvinylpyrrolidone and/or one of the wax binders, preferably carnauba wax, will be present in the core where neither the medicament nor the hydrocolloid gelling agent is compressible and such binder together with the hydrocolloid will form a water-insoluble matrix.

In preferred core formulations, the hydrocolloid gelling agent will be employed in a weight ratio to non-swellable binder and/or wax binder of within the range of from about 5:1 to about 1/5:1 and more preferably from about 3:1 to about 1/3:1.

The sustained release tablets will also include additional edible non-toxic ingredients as conventionally employed in solid medicinal dosage forms. Thus, the core of the tablets of the invention may include one or more excipients in an amount within the range of from about 1% to about 25% by weight and preferably from about 1% to about 10% weight such as lactose, sugar, corn starch, modified corn starch, mannitol, sorbitol, inorganic salts such as calcium carbonate, one or more tableting lubricants in an amount within the range of from about 0.5 to about 8% by weight of the core, and preferably from about 1 to about 4% by weight of the core, such as magnesium stearate, stearic acid, palmitic acid, calcium stearate, talc, carnauba wax and the like. Other conventional ingredients which may optionally be present include preservatives, stabilizers, anti-adherents or silica flow conditioners or glidants, such as Syloid brand silicon dioxide as well as FD&C colors.

The coating layer which is applied over the core, as indicated hereinbefore, will include one or more water-soluble hydrophilic film-formers, binders or barrier materials and one or more relatively water-insoluble hydrophobic barrier materials.

The coating or film layer which is applied over the core will be formed of a mixture of one or more water-soluble hydrophilic polymeric film-formers in an amount within the range of from about 10 to about 90% and preferably from about 10 to about 60% by weight based on the weight of the coating layer and one or more relatively water-insoluble hydrophobic polymeric barrier materials in an amount within the range of from about 10 to about 90% and preferably from about 20 to about 70% by weight of the coating layer. The above mixture of polymers forming the coating layer permits entry of water and hydration of the matrix so that there is not a large initial surge in the release of medicament.

The hydrophilic polymers are water-soluble polymers (under pH 5.5). They include cellulose methyl ethers like methyl cellulose, hydroxypropylmethyl cellulose, hydroxymethyl cellulose phthalate, also hydroxypropyl cellulose, cellulose acetate phthalate or polyvinyl alcohol.

The hydrophobic polymers are slightly soluble in water. (By slightly soluble is meant the definition in USP XIX, page 6, although polymers up to 3% soluble in water can be used.) They include cellulose ethyl esters like ethyl cellulose, also cellulose acetate, polyvinyl alcohol-maleic anhydride copolymers, $\beta$-pinene polymers (Piccolyte), glycerol esters of wood resins like glycerol ester of partially dimerized rosin, glycerol ester of partially hydrogenated wood rosin, glycerol ester of polymerized rosin, hydroxypropyl methyl cellulose phthalate, etc.

Preferred are combinations of methyl cellulose and ethyl cellulose or hydroxypropylmethyl cellulose and ethyl cellulose.

One or more members of each class of polymer can be used in forming the coating material. The weight ratio of hydrophilic polymer or polymers to hydrophobic polymer or polymers is within the range of about 4:1 to about 1:4 (by weight), preferably from about 2:1 to about 1:2, and optimally about 1.5:1 to 1:1. These polymers are best combined in a proportion which results in rupture in about three hours. A film of about 1 to 15 mil. (0.001 to 0.015 inches) preferably 3 to 7 mil., in thickness is sufficient to achieve the purpose.

The combined weight of the components of the core (with the exclusion of the medicament) and coating layer is below about 30% of the weight of the medicament or active drug ingredient present in the core. Finished tablets having a total weight of up to 1 gm or even more can be prepared. Of this total weight, the core will comprise from about 85 to about 98% by weight of the tablet, the coating layer will comprise from about 15 to about 2% by weight of the tablet, with the medicament comprising from about 70 to about 90% or more by weight of the tablet.

The coating or film forming layer will also include one or more plasticizers, such as triethyl citrate, diethyl phthalate, polyethylene glycol (molecular weight 300 to 4000), propylene glycol, glycerin, butyl phthalate, castor oil and the like.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color will be applied together with the film former, plasticizer and solvent composition.

A preferred sustained release tablet in accordance with the present invention will inlucde a core containing from about 80 to about 90% by weight procainamide hydrochloride, from about 15 to about 12% by weight of the hydrocolloid gelling agent which preferably is methyl cellulose and/or hydroxypropylmethyl cellulose, from about 2 to about 5% by weight of polyvinyl pyrrolidone, from about 2 to about 5% by weight of a flow aid agent which preferably is a silica flow agent, and from about 1 to about 4% by weight of one or more tabletting lubricants which preferably is a mixture of magnesium stearate and stearic acid (all of such % being based on the weight of the core) and a coating which contains a mixture of film formers, namely, ethyl cellulose and hydroxypropylmethyl cellulose, and a plasticizer such as triethyl citrate.

The sustained release tablets of the invention may be prepared as follows. Water is added to the medicament, in powdered form, while mixing, for example, in a planetary mixer. The hydrocolloid, non-swellable binder and/or wax are added and mixing is continued. The moist mass is granulated, for example, by forcing through a screen of suitable mesh size. Thereafter, the tabletting lubricant and flow agent, if present, are added and the mixture is thoroughly mixed and then compressed into tablet cores. The coating solution formed of film formers, plasticizers and one or more solvents is then sprayed on the cores to form the tablets of the invention.

The following Examples represent preferred embodiments of the present invention.

EXAMPLE 1

A sustained release formulation capable of slowly releasing the antiarrhythmic agent procainamide hydrochloride for a period of up to 10 to 12 hours or more and having the following composition was prepared as described below.

| Ingredient Core Compostion | Amount (kg) | Per Dosage Unit (mg) |
|---|---|---|
| Procainamide hydrochloride | 10 | 1000 |
| Hydroxypropylmethyl cellulose (Methocel K15M viscosity of 15,000 cps) (hydrophilic polymer) | 1.23 | 123 |
| Polyvinyl pyrrolidone (Plasdone) | 0.38 | 25 |
| Carnauba wax | 0.25 | 25 |
| Silica (glidant) (Syloid 244) | 0.05 | 5 |
| Magnesium stearate (lubricant) | 0.2 | 20 |
| Purified water q.s. | ~300 ml | 25 mg |

| Coating Composition | Amount (g) |
|---|---|
| Hydroxypropylmethyl cellulose (E-5) (hydrophilic polymer) | 12 |
| Ethyl cellulose (Tyme N-22) (hydrophobic film former or binder) | 18 |
| Triethyl citrate (plasticizer) | 1.5 |
| Ethyl alcohol (solvent) q.s. 50:50 Methylene chloride (solvent) q.s. | qs 1 l. |

The q.s. ingredients were for processing purposes only and do not appear in the final product.

The water was added to procainamide hydrochloride while mixing in a planetary (Hobart) mixer until granulated. Then the methyl cellulose, polyvinyl pyrrolidone and carnauba wax were added and the mass was mixed for 5 minutes. The mixture was passed through a 40 mesh screen and thereafter the silica flow agent and magnesium stearate were added thereto. The so-formed mixture was then thoroughly mixed and compressed into tablet cores each weighing 1226 mg.

A coating solution formed of a mixture of hydroxypropylmethyl cellulose, ethyl cellulose and triethyl citrate dissolved in a mixture of ethyl alcohol and methylene chloride was sprayed on the cores to form the sustained release tablets of the invention each weighing 1226 mg and containing 1000 mg procainamide hydrochloride (core=1221 mg).

The so-formed sustained release tablet of the invention was found to undergo substantially zero order release so that it slowly and uniformly releases drug over a 10–12 hour period.

EXAMPLES 2 AND 3

In a manner similar to that described in Example 1, 920 mg tablets each containing 750 mg procainamide hydrochloride and 612 mg tablets each containing 500 mg procainamide hydrochloride were prepared.

EXAMPLE 4

The release rate of active drug determined for the uncoated cores and the film coated tablets prepared according to the procedure of Example 1 by the U.S.P. XX method using Apparatus 2 (paddle, p. 959) at 100 rpm with 0.9 liter of 0.1N HCl at 37° C. as the medium.

TABLE I

| | % Procainamide Released Per Hour | | |
|---|---|---|---|
| | Film Coated Tablet | | |
| Hour | Coating 3% w/w | Coating 6% w/w | Uncoated Core (%) |
| 1 | 7 | 2.5 | 33 |
| 2 | 7.5 | 3 | 15 |
| 3 | 10 | 3.5 | 12 |
| 4 | 9 | 4.5 | 10 |
| 5 | 9 | 3.5 | 9 |
| 6 | 8 | 3.5 | 6 |
| 7 | 8 | 4 | 6 |
| 8 | 6 | 3 | 11 |
| 9 | 6 | 3 | 4 |
| 10 | 7 | 4 | 4 |

EXAMPLES 5 TO 10

Following the procedure of Example 1, tablets of the following composition were prepared.

TABLE II

| | Formula Compositions AMOUNT (% Tab. Wt.) | | | | | |
|---|---|---|---|---|---|---|
| Example No. | 5 | 6 | 7 | 8 | 9 | 10 |
| Procainamide HCl* | 77 | 83 | 91 | 87 | 82 | 83 |
| Hydroxypropyl methyl cellulose (Methocel K-100 M viscosity of 100,000 cps) | 22 | 15 | 8 | 12 | | |
| Hydroxypropyl methyl cellulose (Methocel K-15 M viscosity of 15,000 cps) | | | | | 14 | 10 |
| Carnauba Wax | | | | | | 2.1 |
| Polyvinyl pyrrolidone (Plasdone (PVP)) | | | | | | 3.2 |
| Mg. Stearate | 1 | 1 | 1 | 1 | | 0.8 |
| Stearic Acid | | | | | 1 | |
| Silica flow agent (Syloid 244) | 0.2 | 0.3 | 0.2 | 0.3 | 0.2 | 0.2 |
| TOTAL TAB. WT. (mg) | 1300 | 1200 | 1100 | 1150 | 1215 | 1200 |

*1000 mg Procainamide HCl per tablet. Distilled water added for processing purposes only.

The coating composition for each of the cores of Examples 5 to 10 is similar to that described in Example 1.

EXAMPLES 11 TO 13

Sustained release formulations capable of slowly releasing the antiarrhythmic agent procainamide hydrochloride for a period of up to 10 to 12 hours or more and having the following composition was prepared as described below.

TABLE III

| | Formula Compositions (Batch size 20 tablets) | | |
|---|---|---|---|
| | Amount (gm) | | |
| Example No. | 11 | 12 | 13 |
| Core Composition | | | |
| Procainamide HCl | 10 | 10 | 10 |
| Hydroxypropyl methyl cellulose (Methocel K15-M viscosity of 15,000 cps) | 3.92 | — | — |
| Hydroxypropyl methyl cellulose (Methocel K-100M viscosity of 100,000 cps) | — | 3.92 | — |
| Carboxypolymethylene (Carbopol 934 P) (viscosity 50,000) (swellable binder) | 0.2 | 2.8 | 3.92 |
| Polyvinyl pyrrolidone (Plasdone) (non-swellable binder) | — | — | 0.4 |
| Lactose (Fast Flo) (non-swellable binder) | 0.5 | 0.5 | — |
| Magnesium stearate | 0.3 | 0.3 | 0.3 |
| Silica (glidant) (Syloid 244) | 0.08 | 0.08 | 0.08 |
| Purified water q.s. | 0.2 | 0.2 | 0.2 |
| Coating composition | | | |
| As per Example 1 | | | |

The water was added to procainamide while mixing in a planetary (Hobart) mixer until granulated. Then the carboxypolymethylene was added with mixing. The mixture was passed through a 40 mesh screen and then other hydrocolloid gelling agents were added. The mixture was again passed through a 40 mesh screen and thereafter the silica flow agent and magnesium stearate were added. The so-formed mixture was then thoroughly mixed and compressed into tablet cores each weighing 1226 mg. The tablet cores were then coated as described in Example 1.

EXAMPLE 14

A captopril tablet in accordance with the present invention is prepared following the procedure of Example 1 except substituting 0.5 kg (50 mg per unit) captopril for the procainamide hydrochloride.

EXAMPLE 15

A propranolol tablet in accordance with the present invention is prepared following the procedure of Examples 5 except substituting 0.8 kg (40 mg per unit) of propranolol for the procainamide hydrochloride.

EXAMPLE 16

A fluphenazine HCl tablet in accordance with the present invention is prepared following the procedure of Example 7 except substituting 0.5 kg (10 mg per unit) of fluphenazine HCl for the procainamide hydrochloride.

EXAMPLE 17

An aspirin tablet in accordance with the present invention is prepared following the procedure of Example 9 except substituting 0.7 kg (325 mg per unit) of aspirin for the procainamide hydrochloride.

EXAMPLE 18

A theophylline tablet in accordance with the present invention is prepared following the procedure of Example 11 except substituting 0.6 kg (200 mg per unit) of theophylline for the procainamide hydrochloride.

What is claimed is:

1. In a controlled release procainamide hydrochloride formulation in the form of a tablet, which is adapted to approach zero order release of procainamide hydrochloride over an 8 to 12 hour or more period, which tablet is comprised of a core containing procainamide hydrochloride and a pharmaceutically acceptable coating therefor, the improvement which comprises incorporating in said core from about 5 to about 15% by weight of one or more hydrocolloid gelling agents having a viscosity of within the range of from about 10,000 to about 200,000 centipoises in 2% solution of 20° C. and are selected from the group consisting of cellulose ethers, cellulose alkyl hydroxylates, cellulose alkyl carboxylates, alkali metal salts of cellulose alkyl carboxylates, gum acacia, guar gum, gum tragacanth, gum xanthan, an alkali metal or alkaline earth metal carageenate, an alginate and mixtures thereof, from 0 to about 8% by weight of one or more non-swellable binders, and from 0 to about 8% by weight of one or more wax-binders and said coating comprises a mixture of at least one hydrophilic polymer and at least one hydrophobic polymer in a weight ratio to each other of within the range of from about 4:1 to about 1:4, and said procainamide hydrochloride is present in said core in an amount of from about 80 to about 95% by weight of the core, which represents an increase in procainamide hydrochloride tablet content of at least about 14% over prior known formulations, the combination of said core and coating providing substantially zero order release of said procainamide hydrochloride.

2. The tablet as defined in claim 1 wherein said core contains procainamide hydrochloride in an amount within the range of from about 87 to about 95% by weight of said core.

3. The tablet as defined in claim 1 wherein said hydrocolloid is methyl cellulose, hydroxypropyl cellulose, hydroxypropylmethyl cellulose, carboxypolymethylene, or a mixture of two or more of such hydrocolloids.

4. The tablet as defined in claim 1 including a non-swellable binder or wax binder.

5. The tablet as defined in claim 4 wherein said non-swellable binder is polyvinyl pyrrolidone.

6. The tablet as defined in claim 4 wherein said wax binder is carnauba wax.

7. The tablet as defined in claim 1 wherein said core includes an anti-adherent and a lubricant.

8. The tablet as defined in claim 1 wherein the coating includes one or more plasticizers.

9. The tablet as defined in claim 6 wherein the lubricant is a mixture of magnesium stearate and stearic acid, the gelling agent includes methyl cellulose and/or hydroxypropylmethyl cellulose, and further including silica as an anti-adherent.

10. The tablet as defined in claim 6 wherein the coating includes hydroxypropylmethyl cellulose and ethyl cellulose as a film former and triethyl citrate as a plasticizer.

11. The tablet as defined in claim 4 wherein the hydrocolloid gelling agent is employed in a weight ratio to the non-swellable binder or wax binder of within the range of from about 5:1 to about 1/5:1.

12. The tablet as defined in claim 4 wherein the core contains from about 5 to about 12% by weight hydrocolloid gelling agent and from about 2 to about 5% by weight non-swellable binder or from about 2 to about 5% by weight wax binder.

13. The tablet as defined in claim 4 wherein the non-swellable binder is polyvinyl pyrrolidone, lactose, gelatin, a starch, a sugar or gum acacia.

14. The tablet as defined in claim 4 wherein the wax binder is carnauba wax, paraffin, spermaceti, polyethylene or microcrystalline wax.

15. The tablet as defined in claim 1 wherein the coating layer includes from about 10 to about 90% by weight hydrophilic polymer and from about 90 to about 10% by weight hydrophobic polymer, said % being based on the weight of the coating layer.

16. The tablet as defined in claim 1 where in said core, said hydrocolloid gelling agent is hydroxypropylmethyl cellulose, said non-swellable binder, if present, is polyvinyl pyrrolidone or lactose, and said wax binder, if present, is carnauba wax, and where in said coating said hydrophilic polymer is hydroxypropylmethyl cellulose and said hydrophobic polymer is ethyl cellulose.

* * * * *